US011412989B2

(12) United States Patent
Wijshoff et al.

(10) Patent No.: US 11,412,989 B2
(45) Date of Patent: Aug. 16, 2022

(54) SENSOR DEVICE AND METHOD FOR SENSING PHYSIOLOGICAL INFORMATION OF A SUBJECT

(71) Applicant: KONINKLIJKE PHILIPS N.V., Eindhoven (NL)

(72) Inventors: Ralph Wilhelm Christianus Gemma Rosa Wijshoff, Munstergeleen (NL); Jens Muehlsteff, Aachen (DE); Olaf Such, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 620 days.

(21) Appl. No.: 16/474,909

(22) PCT Filed: Jan. 2, 2018

(86) PCT No.: PCT/EP2018/050066
§ 371 (c)(1),
(2) Date: Jun. 28, 2019

(87) PCT Pub. No.: WO2018/127491
PCT Pub. Date: Jul. 12, 2018

(65) Prior Publication Data
US 2019/0328333 A1 Oct. 31, 2019

(30) Foreign Application Priority Data

Jan. 4, 2017 (EP) .................................. 17150265

(51) Int. Cl.
*A61B 5/1455* (2006.01)
*A61B 5/00* (2006.01)

(52) U.S. Cl.
CPC ............ *A61B 5/721* (2013.01); *A61B 5/1455* (2013.01); *A61B 5/7228* (2013.01); *A61B 2560/0257* (2013.01); *A61B 2562/0219* (2013.01)

(58) Field of Classification Search
CPC . A61B 5/0205; A61B 5/1455; A61B 5/14551; A61B 5/14552; A61B 5/721;
(Continued)

(56) References Cited

U.S. PATENT DOCUMENTS 5,249,576 A 10/1993 Goldberger et al.
5,692,505 A 12/1997 Fouts
(Continued)

FOREIGN PATENT DOCUMENTS

EP 2229880 A1 9/2010

OTHER PUBLICATIONS

H. H. Asada, P. Shaltis, A. Reisner, S. Rhee, and R. C. Hutchinson, "Mobile monitoring with wearable photoplethysmographic biosensors.," IEEE Eng. Med. Biol. Mag., vol. 22, No. 3, pp. 28-40, 2003.
(Continued)

*Primary Examiner* — Chu Chuan Liu

(57) ABSTRACT

The present invention relates to a sensor device and method for obtaining physiological information of a subject. The sensor device comprises a PPG sensor (20), a motion sensor (30) and a device (10) for obtaining physiological information of the subject. The device comprises a processing unit (13) for generating an output signal carrying physiological information by (i) modulating the motion reference signal on a carrier signal of the first set of carrier signals or on a second carrier signal orthogonal to the first set of carrier signals to obtain a modulated signal and combining the modulated signal with the modulated PPG signals to obtain the output signal or (ii) demodulating the modulated PPG
(Continued)

signals, performing artifact-reduction on the demodulated PPG signals using the motion reference signal to obtain artifact-reduced PPG signals and modulating the artifact-reduced PPG signals on the first set of carrier signals to obtain the output signal.

13 Claims, 7 Drawing Sheets

(58) Field of Classification Search
CPC . A61B 5/7228; A61B 5/7207; A61B 5/02416; A61B 5/681; A61B 5/6831; A61B 5/3826; A61B 2562/0219; A61B 2562/0257
See application file for complete search history.

(56) References Cited

U.S. PATENT DOCUMENTS

| | | | |
|---|---|---|---|
| 7,623,990 B2* | 11/2009 | Anderson | A61B 5/14551 702/191 |
| 9,311,825 B2 | 4/2016 | Lusted et al. | |
| 2003/0065269 A1 | 4/2003 | Vetter et al. | |
| 2014/0213863 A1 | 7/2014 | Loseu et al. | |
| 2015/0229341 A1* | 8/2015 | Fung | A61B 5/7207 702/191 |
| 2016/0206247 A1 | 7/2016 | Morland et al. | |

OTHER PUBLICATIONS

J. Allen, "Photoplethysmography and its application in clinical physiological measurement.," Physiol. Meas., vol. 28, No. 3, pp. R1-39, Mar. 2007.
T. Tamura, Y. Maeda, M. Sekine, and M. Yoshida, "Wearable Photoplethysmographic Sensors—Past and Present," Electronics, vol. 3, No. 2, pp. 282-302, Apr. 2014.
G. J. Balady, R. Arena, K. Sietsema, J. Myers, L. Coke, G. F. Fletcher, D. Forman, B. Franklin, M. Guazzi, M. Gulati, S. J. Keteyian, C. J. Lavie, R. Macko, D. Mancini, and R. V Milani, "Clinician's Guide to cardiopulmonary exercise testing in adults: a scientific statement from the American Heart Association.," Circulation, vol. 122, No. 2, pp. 191-225, Jul. 2010.
D. E. Forman, J. Myers, C. J. Lavie, M. Guazzi, B. Celli, and R. Arena, "Cardiopulmonary exercise testing: relevant but underused.," Postgrad. Med., vol. 122, No. 6, pp. 68-86, Nov. 2010.
R. W. C. G. R. Wijshoff, T. van der Sar, W. H. Peeters, R. Bezemer, P. Aelen, I. W. F. Paulussen, S. C. M. a Ordelman, A. Venema, P. F. J. van Berkom, R. M. Aarts, P. H. Woerlee, G.-J. Scheffer, and G. J. Noordergraaf, "Detection of a spontaneous pulse in photoplethysmograms during automated cardiopulmonary resuscitation in a porcine model.," Resuscitation, vol. 84, No. 11, pp. 1625-1632, Nov. 2013.
R. W. C. G. R. Wijshoff, A. M. T. M. Asten, W. H. Peeters, R. Bezemer, G. J. Noordergraaf, M. Mischi, and R. M. Aarts, "Photoplethysmography-Based Algorithm for Detection of Cardiogenic Output During Cardiopulmonary Resuscitation," IEEE Trans. Biomed. Eng., vol. 62, No. 3, pp. 909-921, 2015.
J. van Andel, C. Ungureanu, R. Aarts, F. Leijten, and J. Arends, "Using photoplethysmography in heart rate monitoring at patients with epilepsy," Epilepsy Behav., pp. 1-4, 2015.
W. J. C. van Elmpt, T. M. E. Nijsen, P. A. M. Griep, and J. B. A. M. Arends, "A model of heart rate changes to detect seizures in severe epilepsy," Seizure, vol. 15, No. 6, pp. 366-375, 2006.
X. Schäfer and J. Vagedes, "How accurate is pulse rate variability as an estimate of heart rate variability? A review on studies comparing photoplethysmographic technology with an electrocardiogram.," Int. J. Cardiol., vol. 166, No. 1, pp. 15-29, Jun. 2013.
P. Rodriguez, A. Luna, I. Candela, R. Mujal, R. Teodorescu, and F. Blaabjerg, "Multiresonant Frequency-Locked Loop for Grid Synchronization of Power Converters Under Distorted Grid Conditions," IEEE Trans. Ind. Electron., vol. 58, No. 1,pp. 127-138, 2011.
M. Ciobotaru, R. Teodorescu, and F. Blaabjerg, "A new single-phase PLL structure based on second order generalized integrator," in Proc. IEEE PESC, 2006, pp. 1-7.
K. Mozdzyhski, K. Ratal, and M. Bobrowska-Rafał, "Application of the second order generalized integrator in digital control systems," Arch. Electr. Eng., vol. 63, No. 3, pp. 423-437, Jan. 2014.
International Search Report and Written Opinion, International Application No. PCT/EP20018/050066, dated Apr. 6, 2018.

* cited by examiner

SENSOR DEVICE AND METHOD FOR SENSING PHYSIOLOGICAL INFORMATION OF A SUBJECT

This application is the U.S. National Phase application under 35 U.S.C. § 371 of International Application No. PCT/EP2018/050066, filed on 2 Jan. 2018, which claims the benefit of European Application Serial No. 17150265.1, filed 4 Jan. 2017. These applications are hereby incorporated by reference herein.

FIELD OF THE INVENTION

The present invention relates to a sensor device for arrangement at a subject's body part and a method for sensing physiological information of a subject.

BACKGROUND OF THE INVENTION

Photoplethysmography (PPG) signals are highly susceptible to motion which hampers their use in, e.g., activities of daily living (ADL), cardiopulmonary exercise testing (CPX), or cardiopulmonary resuscitation (CPR). In ADL, PPG is for instance researched to detect pulse rate changes in patients with epilepsy, as this can indicate seizures. Susceptibility to motion hampers beat-to-beat (inter-beat-interval, IBI) analysis to obtain, e.g., pulse rate variability (PRV). Motion can also affect oxygen saturation (SpO2) measurements, e.g., causing false positive desaturations during CPX. During CPR, motion artifacts due to chest compressions complicate detection of a spontaneous pulse in the signal. A common aspect of motion artifacts in ADL, CPX and CPR is their quasi-periodic nature. For sports monitoring, this is usually circumvented by algorithmic filtering and rejection of entire time spans in the signal, leading to a delay in response and inaccuracies that are not acceptable in clinical settings.

In these situations, an artifact reduction algorithm which uses a motion reference signal can improve the PPG signal quality and its applicability. A motion reference signal can for instance be obtained using an accelerometer and/or a gyroscope and/or a barometric pressure sensor and/or a laser Doppler measurement. Via the artifact reference, the motion artifact can be estimated and then subtracted from the measured PPG signal to obtain an artifact-reduced PPG signal which can be further analyzed by other (existing) algorithms.

US 2016/0206247 A1 discloses systems, methods, apparatuses, and software for providing enhanced measurement and correction of physiological data. In a first example, a physiological measurement system is configured to obtain a measured photoplethysmogram (PPG) for a patient, and obtain a reference signal for the patient measured concurrent with the measured PPG, the reference signal including noise components related to at least motion of the patient. The physiological measurement system also is configured to determine a filtered PPG from the measured PPG using at least an adaptive filter with the reference signal to reduce noise components of the measured PPG, determine a final PPG by spectrally subtracting at least a portion of the noise components of the reference signal from the filtered PPG, and identify one or more physiological metrics of the patient based on the final PPG.

U.S. Pat. No. 5,692,505 discloses a circuit for processing the received signals of a pulse oximeter including adaptive noise cancellation.

SUMMARY OF THE INVENTION

It is an object of the present invention to provide a sensor device for arrangement at a subject's body part for sensing physiological information of the subject and to provide a corresponding method, which enable integrating a motion reference measurement in the sensor device without changing the sensor connector, e.g. for coupling the sensor device with a patient monitor or pulse oximetry front-end.

In a first aspect of the present invention a sensor device for arrangement at a subject's body part for sensing physiological information of the subject is presented, said sensor device comprising:
  a PPG sensor for providing a photoplethysmography, PPG, signals modulated on a first set of one or more carrier signals,
  a motion sensor for providing a motion reference signal representing motion of the body part, at which the sensor device is arranged, and
  a device for obtaining physiological information of the subject, said device comprising:
    a PPG signal input for obtaining the PPG signals,
    a motion signal input for obtaining the motion reference signal, and
    a processing unit for generating an output signal carrying physiological information by
      (i) modulating the motion reference signal on a carrier signal of the first set of carrier signals or on a second carrier signal orthogonal to the first set of carrier signals to obtain a modulated signal and combining the modulated signal with the modulated PPG signals to obtain the output signal or
      (ii) demodulating the modulated PPG signals, performing artifact-reduction on the demodulated PPG signals using the motion reference signal to obtain artifact-reduced PPG signals and modulating the artifact-reduced PPG signals on the first set of carrier signals to obtain the output signal.

In yet further aspects of the present invention, there is provided a corresponding method Preferred embodiments of the invention are defined in the dependent claims. It shall be understood that the claimed method has similar and/or identical preferred embodiments as the claimed sensor device, in particular as defined in the dependent claims and as disclosed herein.

The present invention is based on the idea to have a motion measurement at the site of the PPG measurement, i.e., have a motion measurement integrated in the sensor device (also called "probe" herein), e.g. a PPG probe. This motion measurement is used to estimate the motion frequency, and subsequently estimate the motion artifacts in the PPG signal. Removing the estimated motion artifacts can then recover artifact-reduced PPG signals, which can be analyzed further to determine, e.g., PR, IBIs, and SpO2. Alternatively, the artifact reference can allow identifying motion-related frequency components in the PPG signal frequency spectrum and distinguish them from cardiac-related frequency components. In yet another approach, the motion signal can be used to identify segments of the PPG signal which are corrupted by motion and should not be analyzed.

Thus, according to one aspect of the present invention a sensor device, e.g. a PPG/SpO2 probe, with integrated motion artifact handling is proposed, such that it remains pin-compatible and software compatible with the sockets of the installed base, e.g. the pulse oximetry socket of a patient monitor. This allows for the development of, e.g., a dedicated PPG probe for pulse detection during CPR and offers the possibility to retrofit existing sockets of most pulse oximetry vendors. This also implies that the proposed sensor device is somehow identified, since e.g. software on the electronics in a patient monitor is the same, but the presentation of the acquired data has to be changed. Identification of the sensor device can be done manually or automatically.

In the sensor device an accelerometer, gyroscope, barometric pressure sensor, laser Doppler measurement, or other type of motion measurement is integrated. The related signal processing can be integrated in the sensor device itself or can be provided separately, e.g. in a dedicated device for processing, in a computer or processor, or in a patient monitor. The signal processing comprises various related options, one option including modulating the motion measurements onto the modulated PPG output signal so it can be further analyzed and another option including applying signal processing using the motion measurement as an artifact reference in order to reduce the motion artifacts in the PPG signal and providing modulated artifact-reduced PPG signals at the output which can be further processed (this option mimics the signal coming from a passive, uncorrected sensor).

The present invention thus overcomes several problems. In a number of circumstances having a motion reference signal can be advantageous to remove motion artifacts from PPG signals to enhance applicability and interpretation of these signals. A motion reference signal cannot be easily added to the installed base of pulse oximeters/PPG systems. A motion reference signal can be made available to the installed base by integrating the motion reference in the probe such that the probe connector remains pin-compatible with the existing sockets. To use the feature in the probe, a software solution/update could be made in some of the embodiments. An alternative embodiment may be made fully form-fit-function compatible so that there are no software changes needed to the pulse oximetry unit. This opens up the possibility to sell this device as an upgrade to third party pulse oximeter installations. Further, the motion reference signal is obtained exactly at the site of the PPG/SpO2 measurement. Integrating the motion measurement in the probe prevents adding complexity to the (clinical) workflow, as it does not require adding an additional sensor.

It shall be noted that in the context of the present application "to communicate" shall be understood to include direct transmission of the measured motion signal as well as transmission of the measured motion signal after modulation.

There are various options to implement the processing to obtain the output signal. First options may use a coding channel or a second carrier, which options have similarities in the sense that they do not alter the PPG signal constellation. Hence, these first options include adding the motion information to the existing modulated PPG signal. Second options replace a PPG signal by a motion signal or clean the PPG signals and modulate the cleaned signals again, which options do change the PPG signal constellation. Hence, these second options include incorporating the motion information in the constellation of modulated PPG signals by altering the signal constellation, i.e. replacing a PPG signals, demodulating and cleaning and modulating PPG signals.

According to one particular embodiment said processing unit is configured to modulate the motion reference signal on an available coding channel or on a second carrier signal orthogonal to the first set of carrier signals and combine the modulated motion reference signal with the modulated PPG signals to obtain the output signal.

According to another particular embodiment said processing unit is configured to replace one of the modulated PPG signals by the motion reference signal modulated on the first carrier signal corresponding to the said replaced PPG signal by either not using the first carrier signal to modulate a PPG signal and add the modulated motion reference signal to the remaining modulated PPG signals to obtain the output signal, or by removing the modulated PPG signal and replacing it by the modulated motion reference signal to obtain the output signal.

According to a preferred embodiment said motion signal input is configured to obtain multiple motion reference signals for different directions and said processing unit is configured to modulate and incorporate the multiple motion reference signals into the modulated PPG signals. The motion reference signals may e.g. include three accelerometer signals for the three orthogonal directions in space. Using multiple motion reference signals generally increases the accuracy of the artifact reduction.

In another embodiment said processing unit is configured to merge the multiple motion reference signals into a single one-dimensional motion reference signal and is configured to modulate the said single one-dimensional motion reference signal and incorporate it into the modulated PPG signals. In this way the multiple motion reference signals can be easily transmitted. Merging the multiple motion reference signals may involve adding the instantaneous power of the individual motion signals or transferring the norm of the axes of the multiple motion reference signals.

In another embodiment the motion reference signal may be provided to the monitor via an existing coding channel used to identify the type of sensor connected and/or to determine what calibration curve to use to determine SpO2. The motion signal can be either sent directly over this coding channel, or a modulated version of the motion channel can be sent over this coding channel. In the latter case, the channel can also still be used to code the sensor used and/or the calibration curve needed.

Said PPG signal input may be configured to obtain PPG signals from a sensor device comprising one or more light emitters for emitting light onto the tissue of the subject and a light detector for detecting light, which is transmitted through the tissue and/or which is reflected from the tissue to provide the PPG signal, wherein said processing unit is configured to control the light emitter to emit modulated light that is modulated on the first set of carrier signals or to demodulate the detected light with the first set of carrier signals. The light emitter may e.g. comprise two LEDs for emitting infrared and red light, respectively, and the light detector may be a corresponding photodiode that senses transmitted or reflected light.

Said processing unit may also be configured to determine the first set of carrier signals from the PPG signal and to adapt the second carrier signal to be orthogonal to the first set of carrier signals or to identify a carrier signal out of the first set of carrier signals of which the corresponding PPG signal can be replaced by a motion reference signal. This provides another useful option for transmitting the motion reference signal. Identification of the carrier signal can involve locking to the modulation frequency and adjusting to the modulation phase of one of the two modulated PPG signals.

In another embodiment said processing unit is configured to perform artifact-reduction of the demodulated PPG signals by use of correlation cancellation using the motion reference signals to obtain artifact-reduced PPG signals. Hereby, the correlation cancellation may be performed by constructing quadrature motion reference signals, using the phases of quadrature motion reference signals in a quadrature harmonic model combined with a gating function for activation of the estimation of motion artifacts and the subtraction of the motion artifact estimates from the PPG signals. This represents an implementation that can be practically used and that provides reasonable results.

Said processing unit may also be configured to track the frequency of motion in the motion reference signal using a second-order generalized integrator with a frequency-locked loop, FFL, wherein the adaption speed of the second-order generalized integrator and the frequency-locked loop are determined by an integrator time constant and an FFL gain. Hereby, said processing unit is configured to use a fixed integrator time constant and a fixed FFL gain or to use an adaptive integrator time constant and an adaptive FFL gain, wherein the adaptive integrator time constant and the adaptive FFL gain are increased and reduced with time, respectively. This represents another implementation that can be practically used and that provides reasonable results.

The proposed sensor device for arrangement at a subject's body part for sensing physiological information of the subject generally comprises a PPG sensor, a motion sensor, and a device as disclosed herein for obtaining physiological information of the subject based on the modulated PPG signals and the motion reference signal.

The sensor device may further comprise a housing, in which the PPG sensor, the motion sensor and the device are arranged. The sensor device may thus e.g. have the form of a conventional pulse oximeter, e.g. in the form of a finger clip.

The sensor device may further comprise one or more holding components for arrangement of the sensor device at the subject's body. Such holding components may comprise a clamp, an adhesive tape, a belt, a wrist band, etc.

In one embodiment said PPG sensor comprises one or more light emitters for emitting light onto the tissue of the subject and a light detector for detecting light, which is transmitted through the tissue and/or which is reflected from the tissue to provide the PPG signals. Further, said motion sensor may comprise an accelerometer and/or a gyroscope and/or a barometric pressure sensor and/or a laser Doppler measurement.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
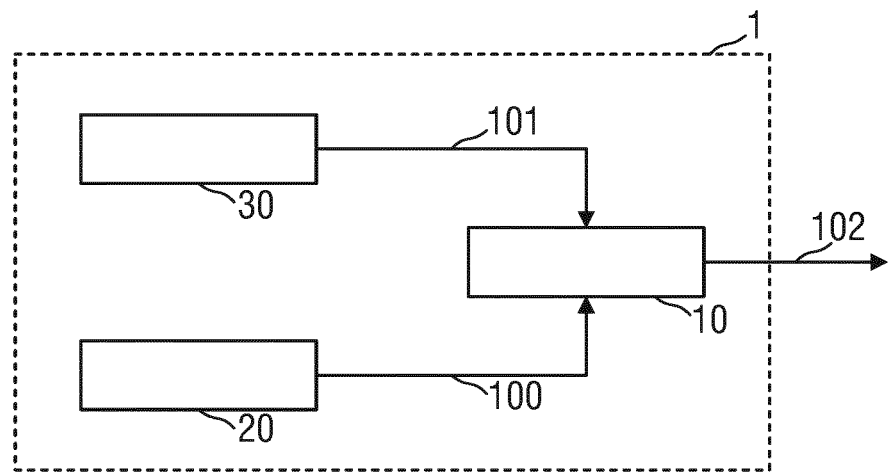
FIG. 1 shows a schematic diagram of the general layout of a sensor device according to the present invention.

FIG. 1 shows a schematic diagram of the general layout of a sensor device 1, also called probe, for arrangement at a subject's body part for sensing physiological information of the subject according to the present invention. The sensor device 1 comprises a PPG sensor 20 for providing a PPG signals 100 modulated on a first set of carrier signals. In an embodiment the PPG sensor 20 may comprise optics to perform PPG measurements, e.g. one or more LEDs 21 (as e.g. shown in FIG. 3) at one or more wavelengths, and one or more photodiodes 22 (as e.g. shown in FIG. 3) sensitive for one or more wavelength ranges.

The sensor device 1 further comprises a motion sensor 30 for providing a motion reference signal 101 representing motion of the body part, at which the sensor device is arranged. In an embodiment the motion sensor may comprise a tri-axial accelerometer and/or a gyroscope and/or a barometric pressure sensor and/or a laser Doppler measurement for acquiring a motion reference measurement.

Still further, the sensor device 1 comprises a device 10 for obtaining physiological information of the subject based on the modulated PPG signals and the motion reference signal. In an embodiment the device 10 may comprise hard- and/or software for merging the measured PPG signals 100 and motion reference signals 101 into a single output signal 102 such that the probe is pin-compatible with existing PPG/SpO2 sockets in the installed base of photoplethysmography or pulse oximeters.

Figure 2:
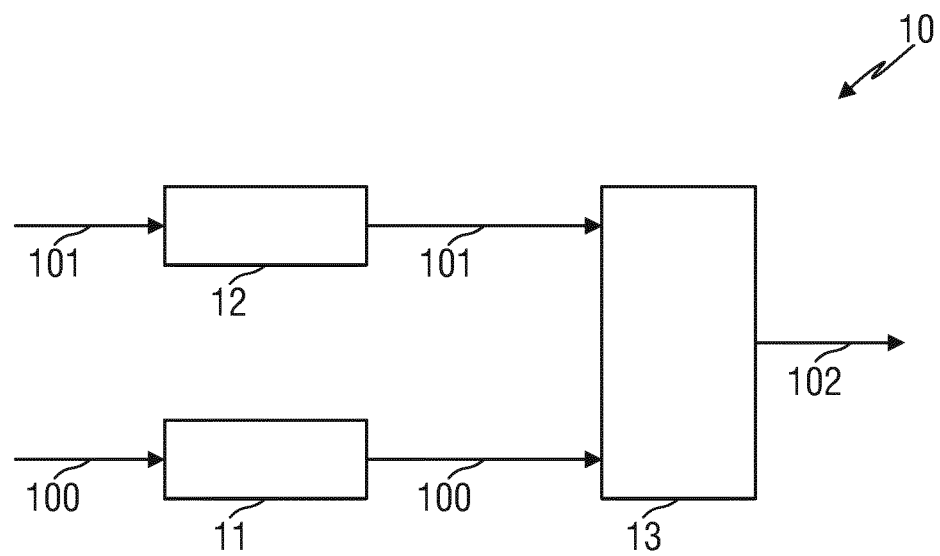
FIG. 2 shows a schematic diagram of the general layout of a device according to the present invention.

FIG. 2 shows a schematic diagram of the general layout of a device 10 for obtaining physiological information of a subject according to the present invention. The device 10 generally comprises a PPG signal input 11 for obtaining PPG signals 100 modulated on a first set of one or more carrier signals. Said PPG signals 100 are provided by the sensor device 1 arranged at a body part of the subject, e.g. an SpO2 probe arranged at a finger of a patient. The PPG signal input 11 may e.g. be a signal interface coupled with a corresponding signal output of a PPG sensor 20 of the sensor device 1 or may be a data interface of a computer.

The device 10 further comprises a motion signal input 12 for obtaining a motion reference signal 101. Said motion reference signal 101 is provided by the sensor device and represents motion of the body part, at which the sensor device is arranged. The motion signal input 12 may e.g. be a motion signal interface coupled with a corresponding motion signal output of a motion sensor 30 of the sensor device 1 or may be a data interface of a computer.

The device 10 further comprises a processing unit 13 for generating an output signal 102 carrying physiological information from the modulated PPG signals 100 and the motion reference signal 101. The processing unit 13 may e.g. be a processor or computer. There are various configurations of the processing unit 13 provided according to the present invention, which will be explained in detail below.

The device 10 may be configured as dedicated device, or may be integrated into the sensor device 1 or another device to which the sensor device 1 is coupled (e.g. a patient monitor), or may be implemented in software running on a computer or processor of an existing device (e.g. a hospital PC). The further evaluation of the output signal 102 of the device 10, e.g. the computation or extraction of a vital sign, is typically included in a dedicated device, such as a computer or patient monitor or pulse-oximetry front-end. In an embodiment, the evaluation is included in the device 10 as well.

The motion reference signal(s) 101 can be used in different ways in the device 10. In a first option the motion reference signal(s) can be mixed with the modulated PPG signal(s), e.g., by modulating the motion reference signal(s) on carriers at different frequencies than the modulation frequency of the PPG signal and its harmonics. In a second option the measured PPG signals can be demodulated, followed by artifact reduction using the motion reference signals, e.g., via correlation cancellation, which is then followed by applying the initial modulation scheme to the artifact-reduced PPG signals again. The first option is preferred in terms of computational load, but requires a change in the front-end and/or algorithms of the receiving unit. The second option can be applied to make the PPG/SpO2 probe compatible with existing PPG/SpO2 front-ends, which only expect PPG signals from passive probes.

Power to the additional hardware in the probe can be supplied through the existing connection by tapping energy from the connection to the LEDs, or by using an unused cable where applicable, or an existing DC line, which some vendors have defined in their sockets. Alternatively, the additional hardware in the probe can be powered by a battery.

Figure 3:
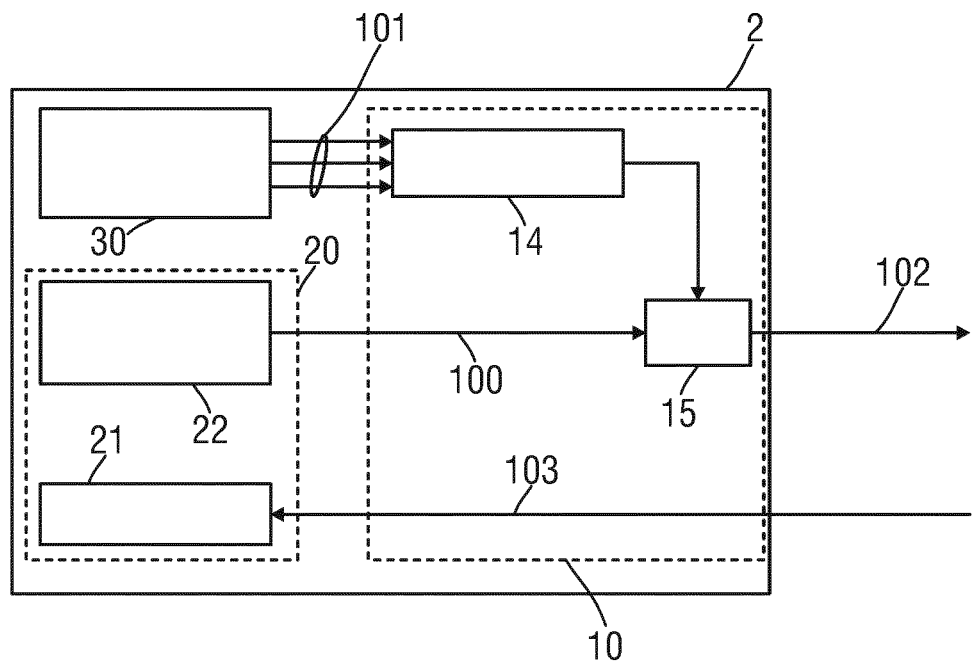
FIG. 3 shows a schematic diagram of a first embodiment of a sensor device according to the present invention.

FIG. 3 shows a schematic diagram of a first embodiment of a sensor device 2 according to the present invention. The sensor device 2 comprises an integrated motion measurement by a tri-axial accelerometer as motion sensor 30. The three (in general multiple) motion reference signals 101 are modulated by a modulator 14 and added by an addition unit 15 (both being part of or implementations of the processing unit 13 of the device 10) onto the output signal 102 of the sensor device 2, i.e., at a different frequency than the modulation frequency of the emitter driving signals 103 (in this embodiment LED drive signals of the light emitters 21). In this way, the sensor device 2 with integrated motion measurement is pin-compatible with existing pulse oximetry sockets. Other modulation schemes may be used as well if they fit the requirements of the hardware of the receiving side.

Alternatively, if the sensor device is only used for pulse detection, and not for SpO2 measurements, only one emitter signal (light signal) is required, e.g. for emitting red or infrared light. In this case, the one-dimensional (1D) motion measurement derived from the accelerometer 30 could replace one of the PPG signals 100 in the modulation scheme. Then the already processed 1D motion signal 101 can be transferred as, e.g., the "red light PPG signal". The connected device, e.g. patient monitor, can automatically recognize the modified sensor device, e.g. via a "coding resistance", and preferably comprises an algorithm for motion compensation and/or identification in modified software.

Figure 4:
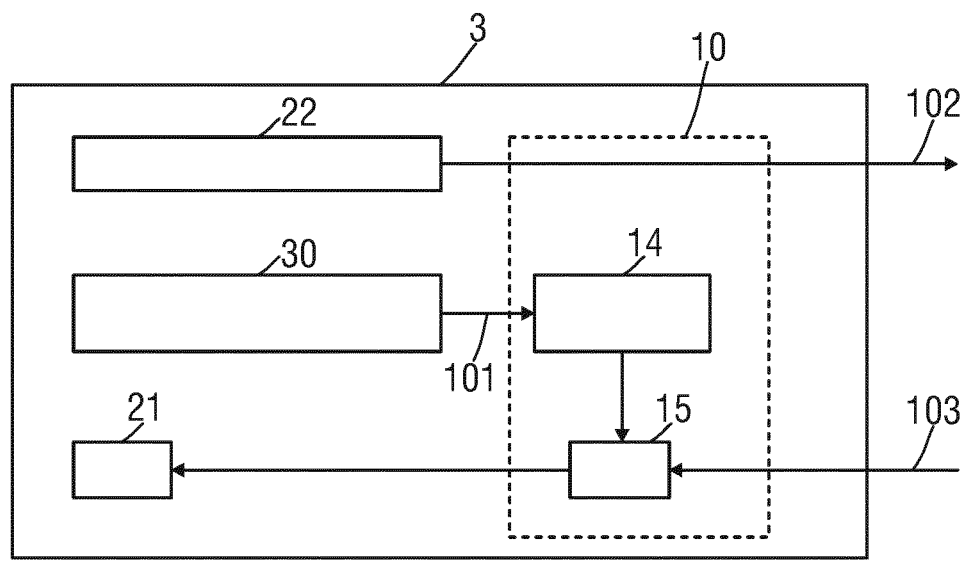
FIG. 4 shows a schematic diagram of a second embodiment of a sensor device.

FIG. 4 shows a schematic diagram of a second embodiment of a sensor device 3. In this embodiment the emitter driving signals (e.g. LED feeding currents) 103 are modulated instead of the output signal 102. Since the probe/tissue combination is a linear system for all matters relevant to this application, a modulation of the output can be equivalently performed at the supply side of the light emitter(s) 21, instead of at the output side. This is particularly of benefit in cases, where the power supply of the additional hardware is derived from these signal lines. Dynamically loading and controllable power supply designs that are able to perform this task are generally known in the art and can be used.

In this embodiment, the modulation scheme of the emitter driving signals is known in the sensor device 3, and the modulation scheme of the motion reference signals 101 has been designed to be compatible with the light emitter modulation scheme. In some embodiments, despite knowing the modulation scheme, the sensor device 3 may still contain hardware and/or software to measure the modulation frequency and modulation phase as needed to properly modulate the motion reference signal.

In a coupled device, e.g. a pulse oximetry front-end, the motion reference signals are demodulated from the output signal 102 to baseband and used to detect, remove or otherwise handle the motion artifacts in the PPG signals. This may require a modification to the front-end receiving algorithms.

Figure 5:
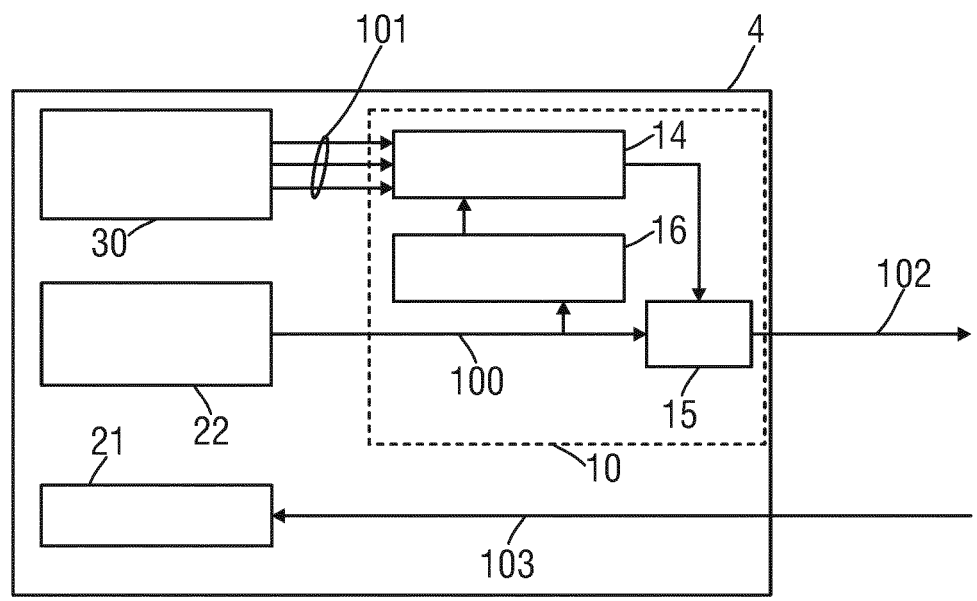
FIG. 5 shows a schematic diagram of a third embodiment of a sensor device according to the present invention.

FIG. 5 shows a schematic diagram of a third embodiment of a sensor device 4 according to the present invention. The sensor device 4 includes an integrated motion measurement by a tri-axial accelerometer 30. The three motion reference signals 101 are adaptively modulated onto the output signal 102 at a different frequency than the modulation frequency of the emitter driving signals 103. In this way, the sensor device 4 is pin-compatible with existing pulse oximetry sockets.

In this embodiment, the modulation scheme of the emitter driving signals 103 is not a-priori known in the sensor device 4. The photodiode signal spectrum, i.e. the spectrum of the PPG signals 100, is analyzed in a spectral analyzer 16 to determine the emitter modulation frequency and select another frequency, which is available for modulation of the motion reference signals 101.

In a coupled device, e.g. a pulse oximetry front-end, the motion reference signals are demodulated to baseband and used to detect, remove or otherwise handle the motion artifacts in the PPG signals. Also this embodiment may require a modification to the front-end receiving algorithms.

Figure 6:
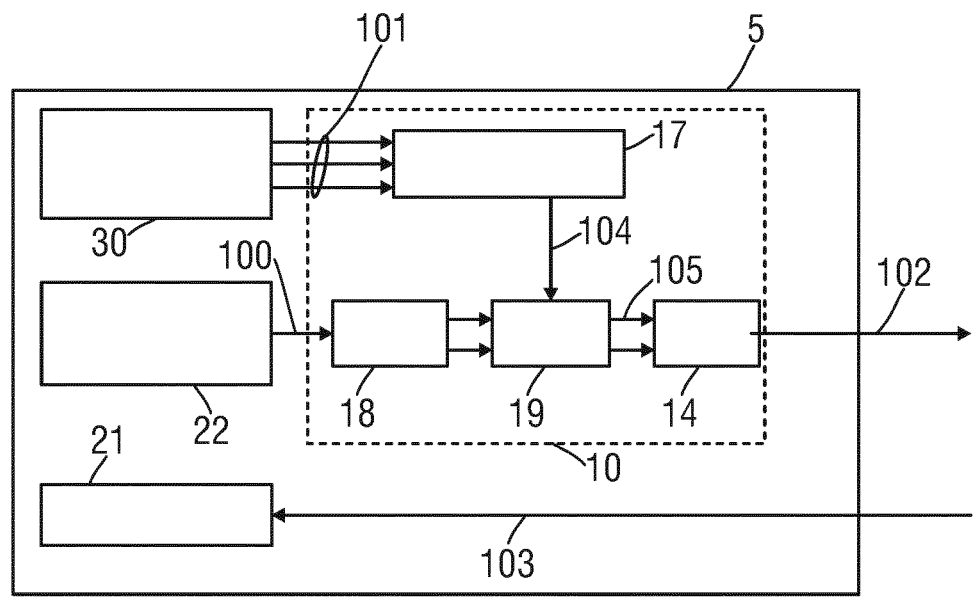
FIG. 6 shows a schematic diagram of a fourth embodiment of a sensor device according to the present invention.

FIG. 6 shows a schematic diagram of a fourth embodiment of a sensor device 5 according to the present invention. The sensor device 5 includes integrated motion artifact reduction. A tri-axial accelerometer 30 is used to measure motion. From the motion reference signals 101 one or more artifact reference signals 104 are derived by a motion artifact reference unit 17. The measured PPG signals 100 are demodulated by a demodulator 18, followed by a motion artifact reduction unit 19, which uses the constructed motion reference signal(s) 104 for motion artifact reduction, e.g. via correlation cancellation. The artifact-reduced PPG signals 105 are then modulated again by modulator 14 to provide an output signal 102 which is compatible with existing pulse oximetry sockets, technology and software.

Figure 12:
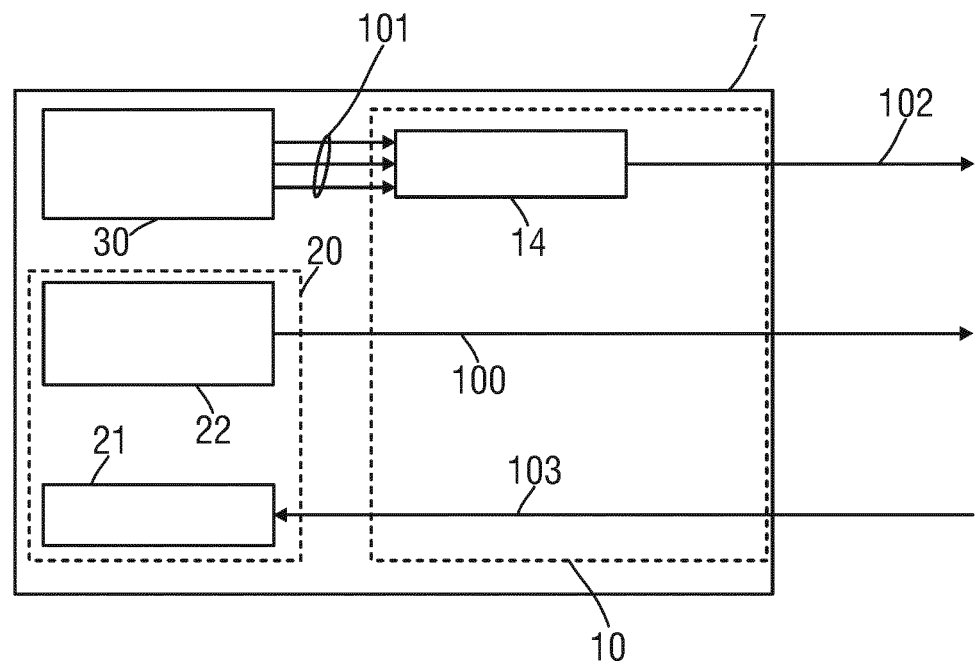
FIG. 12 shows a schematic diagram of a fifth embodiment of a sensor device.

FIG. 12 shows a schematic diagram of a fifth embodiment of a sensor device 7. The sensor device 7 includes an integrated motion measurement. A tri-axial accelerometer 30 is used to measure motion. The individual motion signals 101 are modulated and the modulated signals are sent out as output signals 102 to the pulse oximetry front-end over the coding channel which is typically available in pulse oximetry sensors. These coding channels are typically used to identify the sensor connected and/or to determine what calibration curve to use to measure SpO2. Coding can happen via a resistance value. The modulated motion signals can be sent over this resistance to the pulse oximetry front-end. In this way, the sensor device 7 is pin-compatible with existing pulse oximetry sockets. The connected device, e.g. patient monitor, can automatically recognize the modified sensor device, e.g. via a "coding resistance", and preferably comprises modified software with an algorithm to demodulate the motion reference signals and with an algorithm for motion compensation and/or identification using the motion reference signals. Alternatively, the sensor device 7 may first merge the multiple motion reference signals 101 into a single motion reference signal which can be sent over to the pulse oximetry front-end via the coding channel.

Figure 7:
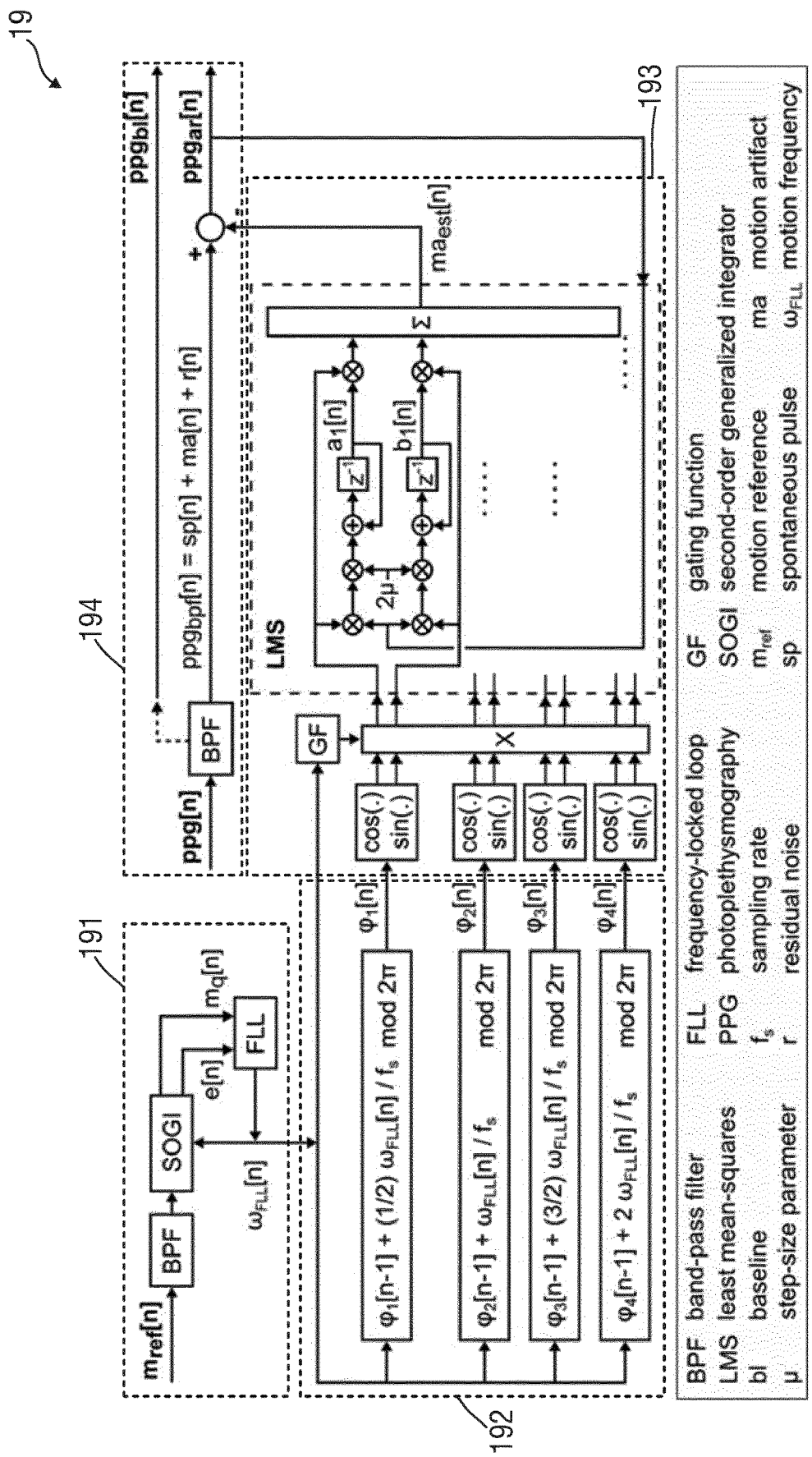
FIG. 7 shows an exemplary circuit diagram of a motion artifact reduction scheme based on correlation cancellation.
Figure 8:
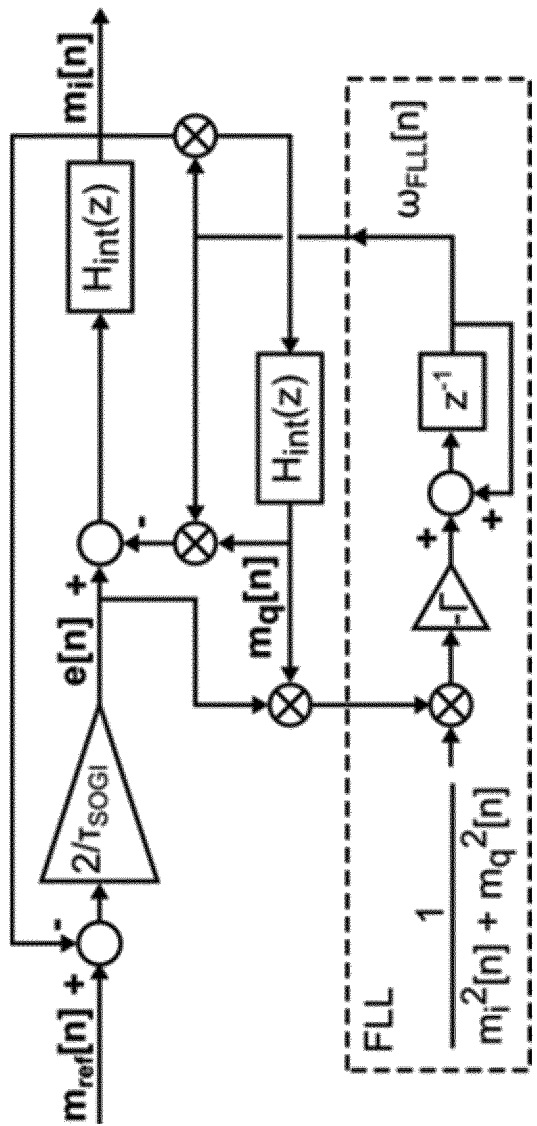
FIG. 8 shows an exemplary circuit diagram of a second-order generalized integrator.

FIG. 7 shows an exemplary circuit diagram of a motion artifact reduction unit 19 based on correlation cancellation. The unit 19 comprises a number of stages. In a first stage 191 it takes a motion reference signal $m_{ref}[n]$, in which it tracks the frequency of motion, $w_{FLL}[n]$. Tracking of motion may be performed using a second-order generalized integrator (SOGI) with a frequency-locked loop (FLL), which is shown in FIG. 8 in an exemplary embodiment. The adaptation speed of the SOGI and FLL are determined by SOGI time constant $\tau_{SOGI}$, and FLL gain $\Gamma$, respectively. Motion reference signal $m_{ref}[n]$ can be derived from a (tri-axial) accelerometer and/or a gyroscope and/or a barometric pressure sensor and/or a laser Doppler measurement.

In a second stage 192 it uses the motion frequency $w_{FLL}[n]$ to construct a number of quadrature motion reference signals. The motion frequency $w_{FLL}[n]$ is used to construct the phases of the quadrature components:

$$\phi_k[n] = \phi_k[n-1] + \frac{k\omega_{FLL}[n]}{2f_s} \mathrm{mod} 2\pi,$$
$$k = 1, 2, 3, 4$$

in which "mod" is the modulo operation and where $\phi_k[n]$ is initialized to 0.

In a third stage 193 these phases are used in a quadrature harmonic model to describe the motion artifact by its estimate $ma_{est}[n]$:

$$ma_{est}[n] = G[n]\sum_{k=1}^{4}[a_k[n]\cos(\phi_k[n]) + b_k[n]\sin(\phi_k[n])]$$

where $G[n]$ is a gating function to switch on and off the artifact estimate, and coefficients $a_k[n]$ and $b_k[n]$ are estimated via a least mean-squares (LMS) algorithm.

The gating function assesses whether artifact reduction can be applied, e.g., by assessing the stability of the motion frequency $w_{FLL}[n]$. If tracking of the motion frequency is sufficiently stable, $G[n]$ equals 1. If tracking of the motion frequency is unstable, $G[n]$ equals 0. Stability of the motion frequency can for instance be assessed via:

$$df_{FLL}[n] = \frac{f_s}{2\pi}H_G(z)|\omega_{FLL}[n] - \omega_{FLL}[n-1]|$$

$$G_h[n] = \begin{cases} 0 \to 1 & \text{if } df_{FLL}[n] < 0.1 \text{ Hz/s} \\ 1 \to 0 & \text{if } df_{FLL}[n] > 0.5 \text{ Hz/s} \end{cases}$$

$$G[n] = H_g(z)G_h[n],$$

$$H_G(z) = \frac{1 - \exp(-1/(\tau_G f_s))}{z - \exp(-1/(\tau_G f_s))}$$

with sampling frequency $f_s$[Hz], and $\tau_G$=0.2 s. The filter $H_G(z)$ is used to track the envelope of the absolute differences of $w_{FLL}[n]$, and to smooth the hysteresis detection $G_h[n]$, where $G_h[n]$ is initialized to 0.

In a fourth stage 194, the motion artifact estimate is subtracted from the measured PPG signal to remove the motion artifact and obtain the artifact-reduced PPG signal $ppg_{ar}[n]$.

Figure 9:
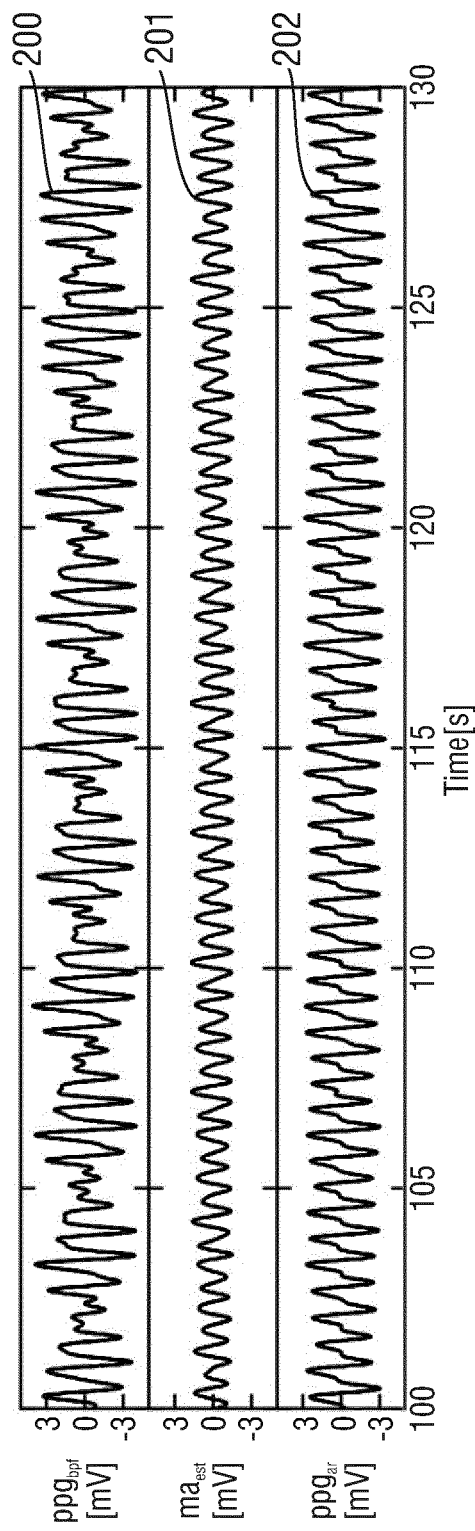
FIG. 9 shows a diagram of various signals in an exemplary circuit diagram of a motion artifact reduction scheme.
Figure 10:
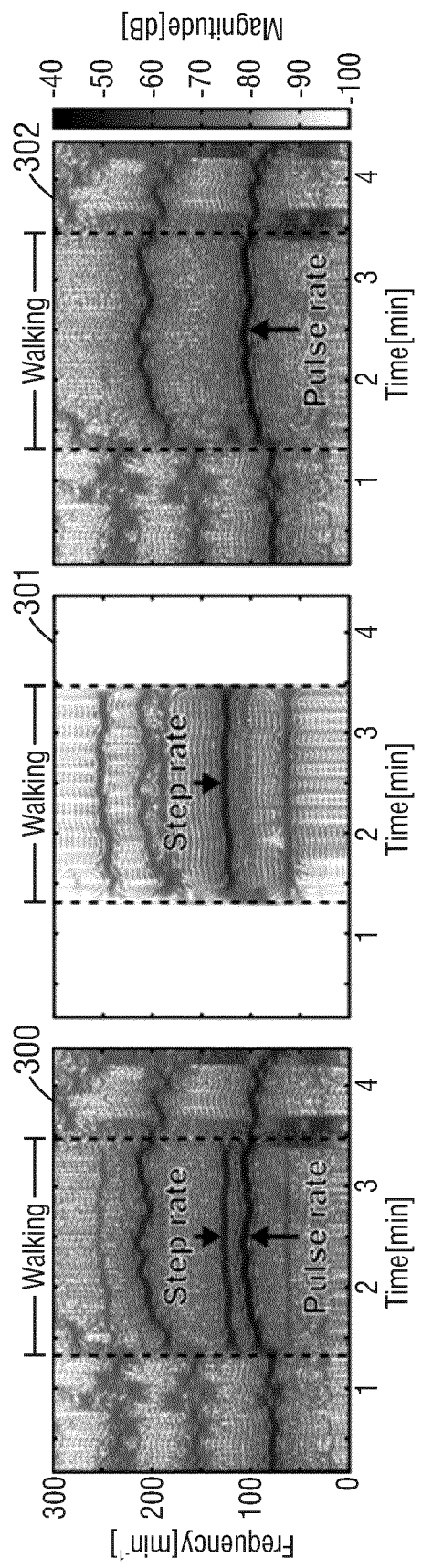
FIG. 10 shows spectrograms illustrating the effectiveness of a motion artifact reduction scheme.

Periodic motion artifacts can be effectively removed by the present invention as illustrated in FIGS. 9 and 10. FIG. 9 shows a diagram of various signals in an exemplary circuit diagram of a motion artifact reduction scheme. FIG. 10 shows spectrograms illustrating the effect of a motion artifact reduction scheme.

FIG. 9 shows a band-pass filtered infrared forehead PPG signal 200 measured while a subject is walking on a treadmill. Motion artifacts cause periodic variation of the PPG signal, where destructive interference by the motion artifacts leads to fading of the signal. The artifact estimate $ma_{est}[n]$ 201 has been derived by using for $m_{ref}[n]$ an accelerometry signal which has been measured on the forehead. Subtracting $ma_{est}[n]$ from the measured PPG signal leads to the artifact-reduced PPG signal 202. The amplitude of the artifact reduced signal is stable.

FIG. 10 shows the spectrograms, which illustrate the effectiveness of artifact removal by the algorithm as used in the motion artifact reduction unit 19 shown in FIG. 7. The spectrograms contain the episode of the PPG signal 200 shown in FIG. 9. FIG. 10 shows the spectrogram 300 of the measured PPG signal 200, in which the pulse rate and the walking-induced frequency components at frequencies related to the step rate are visible. The spectrogram 301 of the motion artifact estimate 201 contains these walking-induced frequency components. The walking-induced frequency components have been removed in the artifact-reduced signal 202, as can be seen in the spectrogram 302 of the artifact-reduced signal 202.

In still another embodiment of a sensor device, e.g. specific for a CPR application where periodic motion artifacts are caused by chest compressions, the artifact reduction algorithm as used in the embodiment of the motion artifact reduction unit 19 shown in FIG. 7 can be adapted for improved performance. Instead of using fixed values for SOGI time constant $\tau_{SOGI}$, and FLL gain $\Gamma$, the parameters can be made adaptive. Initially, when the compression rate is unknown by the system, the parameter $\tau_{SOGI}$ can have a small value and $\Gamma$ can have a large value to speed up learning of the compression rate. Once the algorithm has converged as indicated by a relatively constant $w_{FLL}[n]$, the value of the parameter $\tau_{SOGI}$ can be increased and the value of $\Gamma$ can be reduced to make the filters more narrow and improve the performance.

Figure 11:
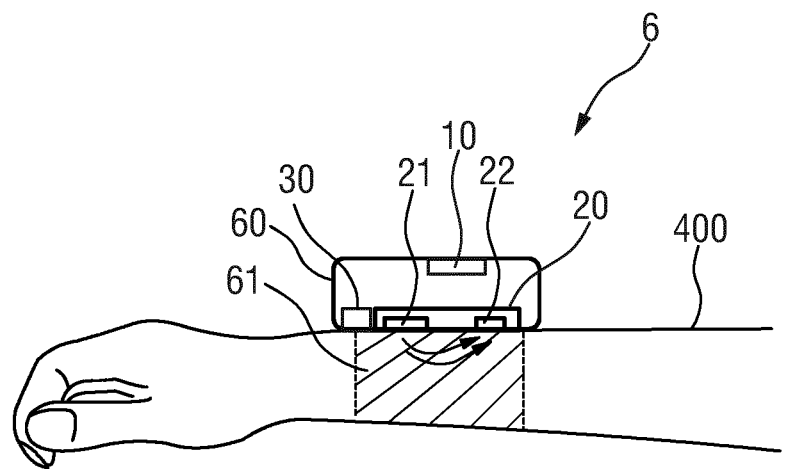
FIG. 11 shows a schematic diagram of an exemplary implementation of a sensor device according to the present invention.

FIG. 11 shows a schematic diagram of an exemplary implementation of a sensor device 6 according to the present invention. In this implementation the sensor device 6 is configured as a wrist-worn device having a housing 60, in which the PPG sensor 20, the motion sensor 30 and the device 10 are arranged. The sensor device 6 further comprises one or more holding components 61, in this case a wrist band, for arrangement of the sensor device 6 at the subject's body 400, in this case a patient's arm. The sensor device can, of course, be implemented differently, e.g. as a finger clip, ear clip, wearable, etc.

The invention applies to existing photoplethysmography and pulse oximeters as the nature of the invention assures pin-compatibility with the existing PPG/SpO2 sockets. The invention can improve applicability of PPG signals e.g. in the context of CPR (e.g., the Philips HeartStart MRx and successor devices), CPX, sports, and ambulatory monitoring (e.g., the Philips IntelliVue MX40 and successors). It can also be applied for pulse oximeters of different manufacturers, thus offering upgrade options to the installed base.

While the invention has been illustrated and described in detail in the drawings and foregoing description, such illustrations and descriptions are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A sensor device for arrangement at a subject's body part for sensing physiological information of the subject, said sensor device comprising:
    a PPG sensor for providing a photoplethysmography, PPG, signals modulated on a first set of one or more carrier signals,
    a motion sensor for providing a motion reference signal representing motion of the body part, at which the sensor device is arranged, and
    a device for obtaining physiological information of the subject, said device comprising:
        a PPG signal input for obtaining the PPG signals,
        a motion signal input for obtaining the motion reference signal, and
        a processing unit for generating an output signal carrying physiological information by:
    (i) modulating the motion reference signal on a carrier signal of the first set of carrier signals or on a second carrier signal orthogonal to the first set of carrier signals to obtain a modulated signal and combining the modulated signal with the modulated PPG signals to obtain the output signal, or
    (ii) demodulating the modulated PPG signals, performing artifact-reduction on the demodulated PPG signals using the motion reference signal to obtain artifact-reduced PPG signals and modulating the artifact-reduced PPG signals on the first set of carrier signals to obtain the output signal.

2. The sensor device as claimed in claim 1,
    wherein said processing unit is configured to replace one of the modulated PPG signals by the motion reference signal modulated on the first carrier signal corresponding to the replaced PPG signal.

3. The sensor device as claimed in claim 1,
    wherein said processing unit is configured to replace one of the modulated PPG signals by the motion reference signal modulated on the first carrier signal corresponding to the said replaced PPG signal by removing the modulated PPG signal and replacing it by the modulated motion reference signal to obtain the output signal.

4. The sensor device as claimed in claim 1,
    wherein said motion signal input is configured to obtain multiple motion reference signals for different directions and said processing unit is configured to modulate and incorporate the multiple motion reference signals into the modulated PPG signals.

5. The sensor device as claimed in claim 4,
    wherein said processing unit is configured to merge the multiple motion reference signals into a single one-dimensional motion reference signal and to modulate the said single one-dimensional motion reference signal and incorporate it into the modulated PPG signals.

6. The sensor device as claimed in claim 1,
    wherein said PPG signal input is configured to obtain PPG signals from a sensor device comprising one or more light emitters for emitting light onto the tissue of the subject and a light detector for detecting light, which is transmitted through the tissue and/or which is reflected from the tissue to provide the PPG signal,
    wherein said processing unit is configured to control the light emitter to emit modulated light that is modulated on the first set of carrier signals or to demodulate the detected light with the first set of carrier signals.

7. The sensor device as claimed in claim 1,
    wherein said processing unit is configured to determine the first set of carrier signals from the PPG signals and to adapt the second carrier signal to be orthogonal to the first set of carrier signals or to identify a carrier signal out of the first set of carrier signals of which the corresponding PPG signal can be replaced by a motion reference signal.

8. The sensor device as claimed in claim 1,
    wherein said processing unit is configured to perform artifact-reduction on the demodulated PPG signals by use of correlation cancellation using the motion reference signals to obtain artifact-reduced PPG signals.

9. The sensor device as claimed in claim 1,
    further comprising a housing, in which the PPG sensor, the motion sensor and the device for obtaining physiological information are arranged.

10. The sensor device as claimed in claim 1,
    further comprising one or more holding components for arrangement of the sensor device at the subject's body.

11. The sensor device as claimed in claim 1,
    wherein said PPG sensor comprises one or more light emitters for emitting light onto the tissue of the subject and a light detector for detecting light, which is transmitted through the tissue and/or which is reflected from the tissue to provide the PPG signals.

12. The sensor device as claimed in claim 1,
    wherein said motion sensor comprises at least one of: an accelerometer, a gyroscope, a barometric pressure sensor, and a laser Doppler measurement.

13. A method for sensing physiological information of a subject by a sensor device arranged at a body part of the subject, said method comprising:
    sensing photoplethysmography, PPG, signals modulated on a first set of one or more carrier signals by the sensor device,
    sensing a motion reference signal by the sensor device, said motion reference signal representing motion of the body part, at which the sensor device is arranged, and
    generating an output signal carrying physiological information by:

(i) modulating the motion reference signal on a carrier signal of the first set of carrier signals or on a second carrier signal orthogonal to the first set of carrier signals to obtain a modulated signal and combining the modulated signal with the modulated PPG signals to obtain the output signal, or
(ii) demodulating the modulated PPG signals, performing artifact-reduction on the demodulated PPG signals using the motion reference signal to obtain artifact-reduced PPG signals and modulating the artifact-reduced PPG signals on the first set of carrier signals to obtain the output signal.

* * * * *